United States Patent
Edwards et al.

(10) Patent No.: US 12,124,325 B2
(45) Date of Patent: Oct. 22, 2024

(54) AUTOMATIC SENSOR TRACE VALIDATION USING MACHINE LEARNING

(71) Applicant: Siemens Healthcare Diagnostics Inc., Tarrytown, NY (US)

(72) Inventors: Mark Edwards, Armonk, NY (US); Vivek Singh, Princeton, NJ (US); Bogdan Georgescu, Princeton, NJ (US); Ankur Kapoor, Plainsboro, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 3 days.

(21) Appl. No.: 17/905,101

(22) PCT Filed: Feb. 25, 2021

(86) PCT No.: PCT/US2021/019731
§ 371 (c)(1),
(2) Date: Aug. 26, 2022

(87) PCT Pub. No.: WO2021/173872
PCT Pub. Date: Sep. 2, 2021

(65) Prior Publication Data
US 2023/0091197 A1    Mar. 23, 2023

Related U.S. Application Data

(60) Provisional application No. 62/982,568, filed on Feb. 27, 2020.

(51) Int. Cl.
G06F 11/07     (2006.01)
G06N 3/0455    (2023.01)
G06N 3/08      (2023.01)

(52) U.S. Cl.
CPC ........ *G06F 11/079* (2013.01); *G06F 11/0721* (2013.01); *G06N 3/0455* (2023.01); *G06N 3/08* (2013.01)

(58) Field of Classification Search
CPC . G06F 11/079; G06F 11/0721; G06N 3/0455; G06N 3/08
See application file for complete search history.

(56) References Cited

U.S. PATENT DOCUMENTS

| | | | |
|---|---|---|---|
| 7,696,866 B2 * | 4/2010 | Horvitz | G06Q 50/06 340/3.7 |
| 11,451,398 B2 * | 9/2022 | Ghanea-Hercock | H04L 9/3239 |

(Continued)

FOREIGN PATENT DOCUMENTS

| CN | 108681747 A | 10/2018 |
|---|---|---|
| CN | 109477748 A | 3/2019 |

(Continued)

OTHER PUBLICATIONS

Pengchen Wei et al: "Statistics and Analysis based on R-language data Digging", University of Electronic Science and Technology of China Press, ISBN 978-7-5647-5409-9, Dec. 31, 2017.

(Continued)

*Primary Examiner* — Matthew M Kim
*Assistant Examiner* — Indranil Chowdhury

(57) ABSTRACT

A computer-implemented method for detecting a failure of a device connected to a sensor is disclosed. The method includes a machine learning model receiving a trace signal from the sensor indicating a status of the device, the machine learning model encoding the trace signal into a plurality of vector representations, and the machine learning model determining whether the trace signal is valid or invalid based on the plurality of vector representations.

21 Claims, 10 Drawing Sheets

(56) References Cited

U.S. PATENT DOCUMENTS

| | | | |
|---|---|---|---|
| 11,519,771 B2* | 12/2022 | Dunfee | G01F 22/02 |
| 2008/0021395 A1 | 1/2008 | Yodfat et al. | |
| 2014/0276566 A1 | 9/2014 | Chandrasenan | |
| 2018/0214634 A1 | 8/2018 | Neftel et al. | |
| 2018/0285233 A1 | 10/2018 | Norrie et al. | |
| 2018/0365089 A1* | 12/2018 | Okanohara | G06F 11/0703 |
| 2019/0354080 A1* | 11/2019 | Yoshida | G06N 20/00 |
| 2020/0089556 A1* | 3/2020 | Chen | G06N 3/08 |
| 2020/0320383 A1 | 10/2020 | Dechu et al. | |
| 2020/0387747 A1* | 12/2020 | Cha | G06F 18/214 |
| 2023/0025238 A1* | 1/2023 | Rudolph | G06N 3/088 |
| 2023/0186078 A1* | 6/2023 | Wang | G06N 3/105 |
| | | | 706/25 |

FOREIGN PATENT DOCUMENTS

| | | | | |
|---|---|---|---|---|
| CN | 109660297 A | 4/2019 | | |
| CN | 110023764 A | 7/2019 | | |
| CN | 110168570 A | 8/2019 | | |
| CN | 110297178 A | 10/2019 | | |
| CN | 110333739 A | 10/2019 | | |
| CN | 110399986 A | 11/2019 | | |
| CN | 110647414 A | 1/2020 | | |
| CN | 110794227 A | 2/2020 | | |
| CN | 115135358 A | 9/2022 | | |
| JP | 2007-140805 A | 6/2007 | | |
| JP | 2007-240328 A | 9/2007 | | |
| JP | 2014-142697 A | 8/2014 | | |
| JP | 2016177829 A | 10/2016 | | |
| JP | 2018-049355 A | 3/2018 | | |
| JP | 2019-139375 A | 8/2019 | | |
| WO | 2017/094267 A1 | 6/2017 | | |
| WO | WO-2018017756 A1 * | 1/2018 | | G01F 22/02 |
| WO | 2018/091746 A1 | 5/2018 | | |
| WO | 2020/000405 A1 | 1/2020 | | |
| WO | WO-2021173872 A1 * | 9/2021 | | G06F 11/0721 |
| WO | WO-2022053163 A1 * | 3/2022 | | |
| WO | WO-2023288230 A1 * | 1/2023 | | G01N 35/1016 |
| WO | WO-2023126828 A1 * | 7/2023 | | |
| WO | WO-2024069024 A1 * | 4/2024 | | G06F 11/2236 |

OTHER PUBLICATIONS

Qi Li et al: "Big data analysis", Chongqing University Press, ISBN 978-7-5689-0043-0, Apr. 30, 2017.

English translation of Chinese Office Action of corresponding Chinese patent Application No. 202180017083.3 16 Pages.

PCT International Search Report and Written Opinion dated May 6, 2021 (11 Pages).

* cited by examiner

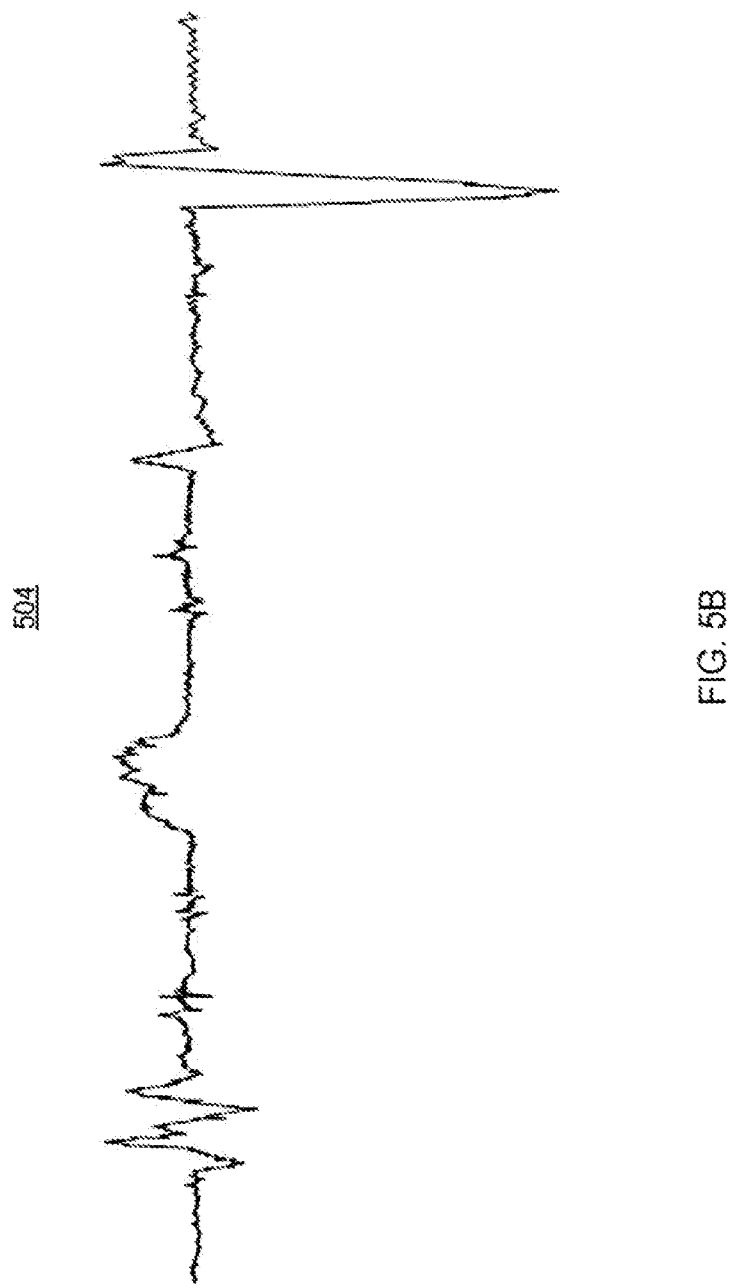

AUTOMATIC SENSOR TRACE VALIDATION USING MACHINE LEARNING

CROSS REFERENCE TO RELATED APPLICATION

This application claims the benefit of U.S. Provisional Patent Application No. 62/982,568, entitled "AUTOMATIC SENSOR TRACE VALIDATION USING MACHINE LEARNING" filed Feb. 27, 2020, the disclosure of which is hereby incorporated by reference in its entirety for all purposes.

TECHNOLOGY FIELD

The present disclosure relates to automatic validation of a sensor trace signal using machine learning techniques. More particularly, the present disclosure relates to a method and a system for detecting a failure of a device through validation of a sensor trace signal.

BACKGROUND

An immunoassay and clinical chemistry analyzer is an integrated machine, which relies on the reliable performance of each individual component. For instance, an aspirate probe is used to aspirate a certain desired volume of a liquid and dispense it. One or more sensors are often provided to validate whether an expected amount of volume is aspirated. If the validation fails on a regular basis, it may suggest that the aspirate probe malfunctions and requires maintenance.

A set of rules specifying safety margins are typically provided to automate the validation process. When a trace signal is beyond the safety margins, the task (e.g., aspiration) may fail. However, these sensors can also potentially collect ambient noises, and thus the algorithmic analysis must be invariant to such noises. To deal with variations caused by the noises, rule engines often become increasingly complex, and gradually become difficult to maintain.

SUMMARY

Embodiments of the present invention address and overcome one or more of the above shortcomings and drawbacks, by providing a method and system of automatically detecting a device failure using sensor trace data.

The disclosure provides a computer-implemented method for detecting a failure of a device, wherein the device is connected to a sensor, the method comprising: receiving, by a machine learning model, a trace signal from the sensor indicating a status of the device; encoding, by the machine learning model, the trace signal into a plurality of vector representations; and determining, by the machine learning model, whether the trace signal is valid or invalid based on the plurality of vector representations.

Embodiments further provide a computer-implemented method, further comprising: reconstructing, by the machine learning model, the trace signal; and highlighting one or more discrepancies between the reconstructed trace signal and the trace signal in a graphical user interface (GUI).

Embodiments further provide a computer-implemented method, further comprising: estimating one or more parameters associated with the device based on the plurality of vector representations.

Embodiments further provide a computer-implemented method, further comprising: regressing the plurality of vector representations to estimate the one or more parameters.

Embodiments further provide a computer-implemented method, wherein the plurality of vector representations is included in a 64-dimensional manifold.

Embodiments further provide a computer-implemented method, further comprising: if the trace signal is invalid, identifying, by the machine learning model, a category of the failure.

Embodiments further provide a computer-implemented method, wherein the machine learning model is a deep neural network.

Embodiments further provide a computer-implemented method, further comprising: receiving, by the machine learning model, a plurality of training trace signals from the sensor; and receiving, by the machine learning model, one or more labelling tags from a human for each training trace signal, wherein the one or more labelling tags indicate whether each training trace signal is valid or invalid.

The disclosure further provides a computer-implemented method for detecting a failure of an aspirate probe, wherein the aspirate probe is connected to a sensor, the method comprising: receiving, by a machine learning model, a trace signal from the sensor indicating a status of the aspirate probe; encoding, by the machine learning model, the trace signal into a plurality of vector representations; and determining, by the machine learning model, whether the trace signal is valid or invalid based on the plurality of vector representations. If the trace signal is invalid, identifying, by the machine learning model, a category of the failure associated with the aspirate probe.

Embodiments further provide a computer-implemented method, further comprising: reconstructing, by the machine learning model, the trace signal; and highlighting one or more discrepancies between the reconstructed trace signal and the trace signal in a graphical user interface (GUI).

Embodiments further provide a computer-implemented method, further comprising: regressing, by the machine learning model, the plurality of vector representations to estimate one or more parameters associated with the aspirate probe.

Embodiments further provide a computer-implemented method, wherein the one or more parameters include a volume aspirated by the aspirate probe, or the number of aspiration operations.

Embodiments further provide a computer-implemented method, wherein the category of the failure is one of no aspiration, no dispensation, and no trace signals.

Embodiments further provide a computer-implemented method, wherein the plurality of vector representations is included in a 64-dimensional manifold.

The disclosure further provides a system for detecting a failure of a device, wherein the device is connected to a sensor, the system comprising: an encoder network for encoding a first trace signal from the sensor into a plurality of vector representations; a decoder network for reconstructing the plurality of vector representations into a second trace signal; and a classification network for identifying whether the first trace signal is valid or invalid.

Embodiments further provide a system, further comprising: a parameter estimation network for estimating one or more parameters associated with the device based on the plurality of vector representations.

Embodiments further provide a system, wherein the one or more parameters are estimated by regressing the plurality of vector representations.

Embodiments further provide a system, wherein the plurality of vector representations is included in a 64-dimensional manifold.

Embodiments further provide a system, wherein the decoder network is further configured for identifying one or more discrepancies between the first trace signal and the second trace signal.

Embodiments further provide a system, wherein the one or more discrepancies are identified based on the second trace signal and a plurality of gradients output from the classification network.

Additional features and advantages of the invention will be made apparent from the following detailed description of illustrative embodiments that proceeds with reference to the accompanying drawings.

BRIEF DESCRIPTION OF THE DRAWING FIGURES

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 5B illustrates a reconstructed trace signal, in accordance with an embodiment described herein;

DETAILED DESCRIPTION

The following disclosure describes the present invention according to several embodiments directed to a method and system of automatically detecting a device failure using sensor trace data. A machine learning model is used to analyze trace signals from one or more sensors connected to a device (e.g., aspirate probe) and determine whether a task (e.g., aspiration) associated with the device is completed as desired. In an embodiment, if the task fails, then the machine learning model can further indicate a cause of the failure. In an embodiment, a deep neural network is used in the machine learning model to reconstruct trace signals, while simultaneously detecting task failures. The deep neural network can highlight one or more portions of the original trace signal which may be indicative of the failure.

Figure 1:
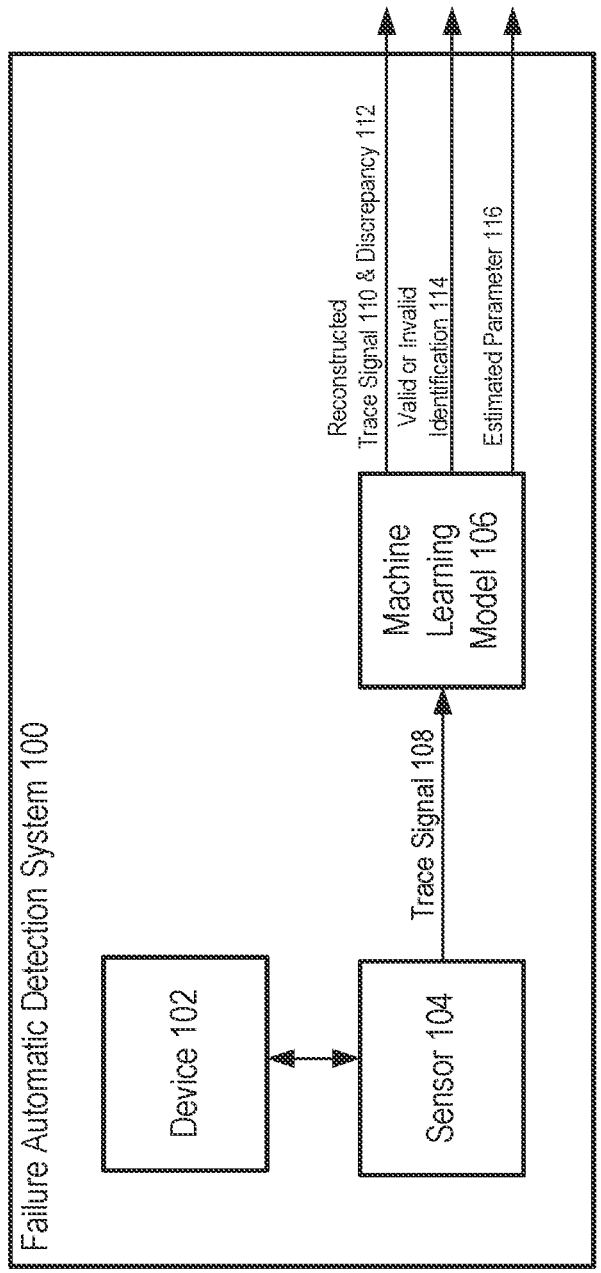
FIG. 1 illustrates a block diagram of the failure automatic detection system, in accordance with an embodiment described herein.

FIG. 1 illustrates a block diagram of a failure automatic detection system 100, in accordance with an embodiment described herein. The failure automatic detection system 100 includes a device 102 (e.g., aspirate probe) for performing a task (e.g., aspiration); a sensor 104 connected to the device 102; and a machine learning model 106 (e.g., deep neural network) trained to identify a failure of the task, and a cause of the failure. The sensor 104 monitors the task performed by the device 102 and generates a trace signal 108, which is input into the machine learning model 106. The machine learning model 106 has been trained by a large number of trace signals including valid trace signals indicative of successful tasks and trace signals indicative of failed tasks. Thus, the trained machine learning model 106 can identify a trace signal 108 indicative of a failed task. In some embodiments, information is provided with the failed trace signals 108 indicating the cause of failure. This information is used to train the machine learning model 106 to further provide a category of the failure (i.e., cause of the failure) when a trace signal 108 is classified as corresponding to a failed task. In an embodiment, the trained machine learning model 106 can identify whether the trace signal 108 is valid or invalid (i.e., failure) 114. In another embodiment, the trained machine learning model 106 can further output a reconstructed trace signal 110. If the reconstructed trace signal 110 is different from the trace signal 108, the trained machine learning model 106 can further create a display of the two trace signals that highlight regions where one or more discrepancies 112 reside. In another embodiment, the trained machine learning model 106 can further output an estimated parameter 116 associated with the device 102, to further support the valid or invalid identification 114. The parameter 116 can be any parameter associated with the function of the device 102. For example, if the device is an aspirate probe, the parameter 116 can be a volume aspirated by the aspirate probe, or the number of aspiration operations, etc.

In general, the sensor 104 can be any sensor which can monitor a task performed by the device 102, e.g., a pressure sensor, a temperature sensor, or a voltage sensor, etc. A trace signal 108 is output from the sensor 104 and input into the machine learning model 106.

Figure 2:
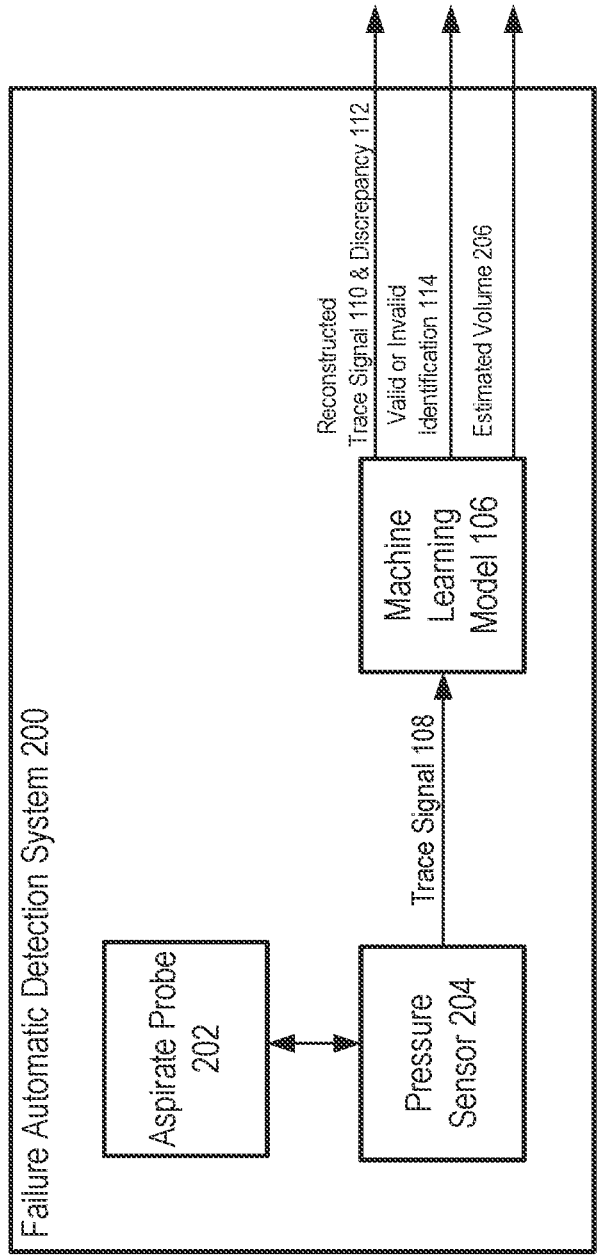
FIG. 2 illustrates a block diagram of the failure automatic detection system, in accordance with another embodiment described herein.
Figure 3:
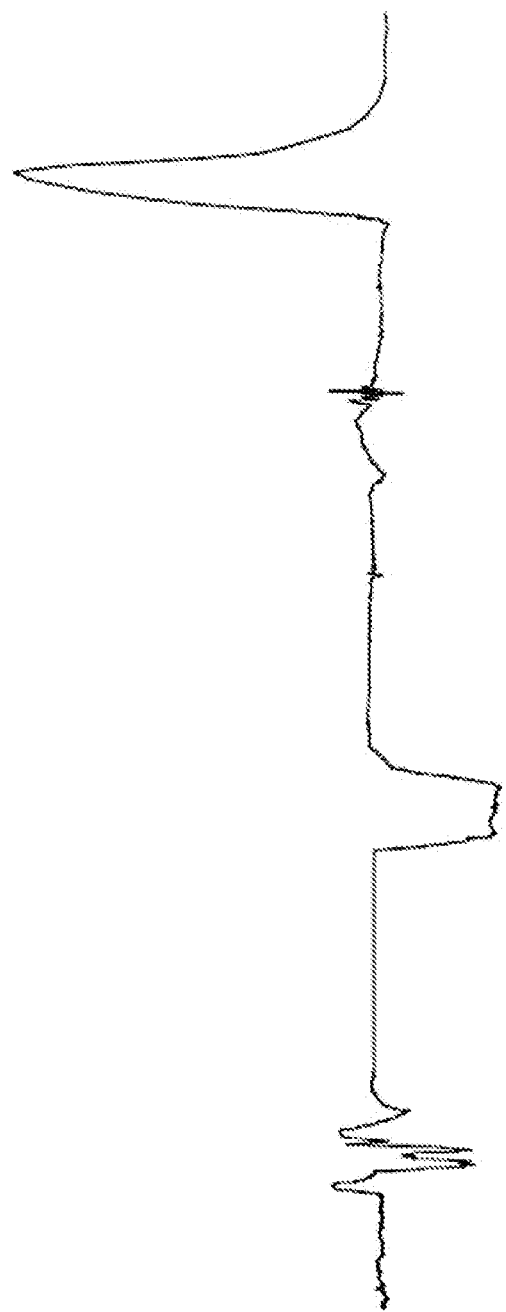
FIG. 3 illustrates a valid sample trace signal from a sensor connected to an aspirator probe, in accordance with an embodiment described herein.

FIG. 2 illustrates a block diagram of the failure automatic detection system 200, in accordance with another embodiment described herein. The failure automatic detection system 200 includes an aspirate probe 202 for performing an aspiration task; a pressure sensor 204 connected to the aspirate probe 202; and a machine learning model 106 (e.g., deep neural network) trained to identify a failure of the aspiration, and a cause of the failure. The pressure sensor 204 monitors aspiration operations by the aspirate probe 202 and generates a trace signal 108, which is input into the trained machine learning model 106. The trained machine learning model 106 can identify a trace signal 108 indicative of a failed aspiration and category of the failure (e.g., no aspiration occurs; no dispensation occurs; no trace signals observed, etc.). In an embodiment, the trained machine learning model 106 can identify whether the trace signal 108 is valid or invalid (i.e., indicative of failure) 114. In another embodiment, the trained machine learning model 106 can further output a reconstructed trace signal 110, together with one or more discrepancies 112 in case of a failure. In another embodiment, the trained machine learning model 106 can further output an estimated volume 206 aspirated by the aspirate probe 202. FIG. 3 illustrates a valid sample trace signal from a sensor connected to the aspirate probe 202, in accordance with an embodiment described herein. The sample trace signal can include time-series measured data collected from any sensor (e.g., the pressure sensor 204).

Figure 4:
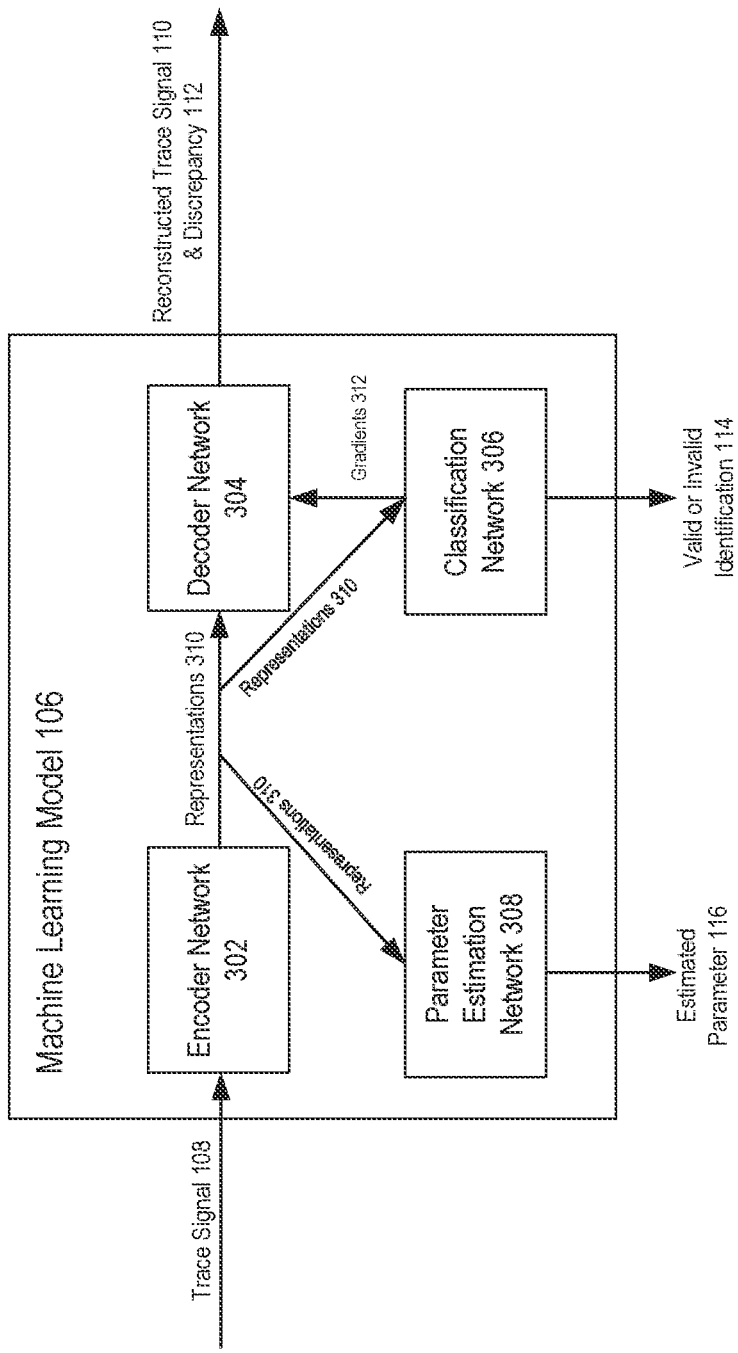
FIG. 4 illustrates a block diagram of a machine learning model, in accordance with an embodiment described herein.
Figure 5A:
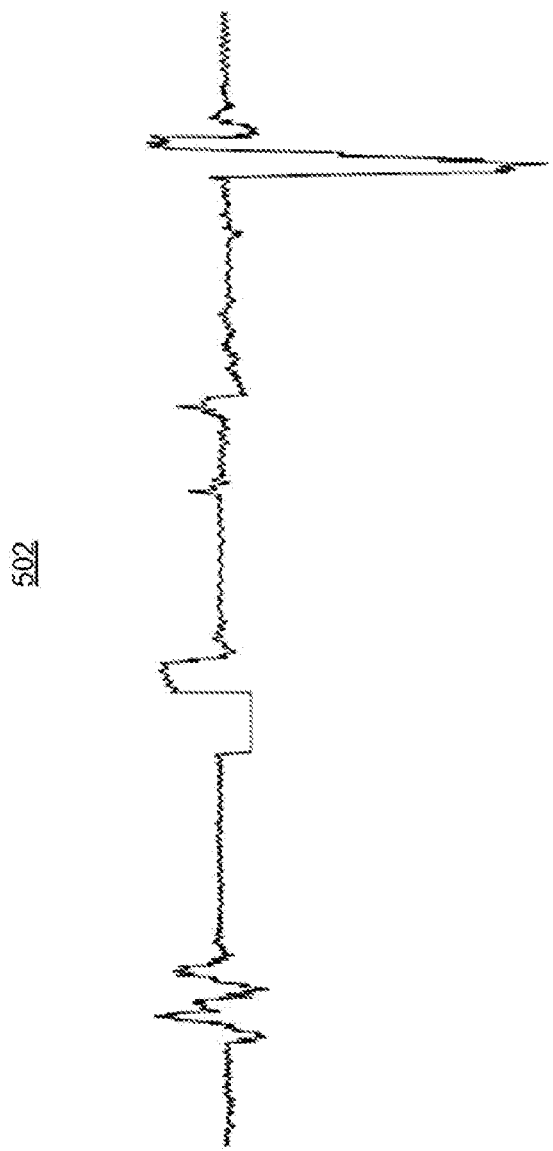
FIG. 5A illustrates an original trace signal indicative of a failure, in accordance with an embodiment described herein.
Figure 5C:
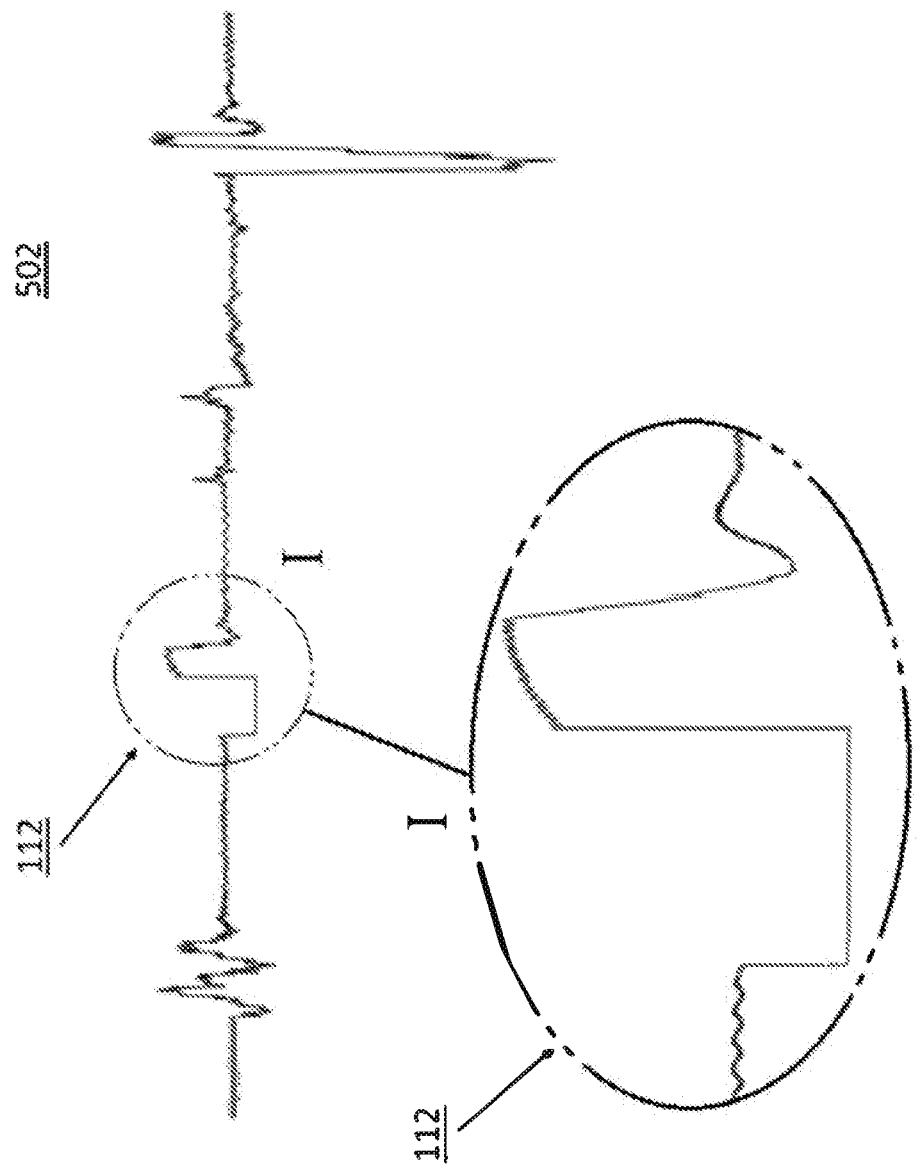
FIG. 5C illustrates an original trace signal highlighting a discrepancy between the original trace signal and the reconstructed trace signal, in accordance with an embodiment described herein.

FIG. 4 illustrates a block diagram of the machine learning model 106, in accordance with an embodiment described herein. In this embodiment, the machine learning model 106 is implemented as a deep neural network. As is generally understood in the art, the term "deep neural network" refers to an artificial neural network that uses multiple layers to progressively extract higher-level features from input data. The machine learning model 106 shown in FIG. 4 includes an encoder network 302, a decoder network 304, a classification network 306, and a parameter estimation network 308. In this example, the encoder network 302 encodes the trace signal 108 into one or more compact representations 310. In one embodiment, the compact representations 310 comprise a 64-dimensional manifold. The representations 310 are used in other networks 304, 306, and 308 for trace signal reconstruction, failure identification, and parameter estimation, respectively. In an embodiment, the representations 310 can be input to the classification network 306 to classify the trace signal 108 as a valid or invalid trace signal. In a further embodiment, the representations 310 can be input to the decoder network 304 to reconstruct a trace signal 110. If the trace signal 108 is identified as an invalid signal, then the reconstructed trace signal 110 is different from the original trace signal 108. One or more discrepancies 112 between the reconstructed trace signal 110 and the original trace signal 108 are highlighted in a display. For example, in one embodiment, the reconstructed trace signal 110 and the original trace signal 108 are displayed in a graphical user interface (GUI) and the discrepancies 112 are shown in red color, so that the user can be notified of the failure and quickly locate the possible failure cause. The discrepancies 112 can be identified and highlighted based on the reconstructed trace signal 110 from the decoder network 304 and gradients 312 from the classification network 306. Conventional backpropagation techniques may be used to compute gradients 312 in a classification network 306 more efficiently. FIG. 5A illustrates an original trace signal 502 indicative of a failure, in accordance with an embodiment described herein. FIG. 5B illustrates a reconstructed trace signal 504, in accordance with an embodiment described herein. FIG. 5C illustrates the original trace signal 502 highlighting a discrepancy 112 between the original trace signal and the reconstructed trace signal, in accordance with an embodiment described herein.

Continuing with the example machine learning model 106 of FIG. 4, the representations 310 are input to the parameter estimation network 308 for parameter estimation. For example, where a machine learning model 106 is included in the failure automatic detection system 200 with the aspirate probe 202, the parameter estimation network 308 can regress the representations 310 to obtain an estimated parameter 116 (e.g., estimated volume 206 aspirated by the aspirate probe 202). The estimated volume 206 is compared with an expected volume. If the difference between the estimated volume and the expected volume is over a predefined threshold, then the aspiration is considered a failure. If the difference between the estimated volume and the expected volume is within the predefined threshold, then it can be concluded that a sufficient volume has been aspirated, irrespective of ambient noises that may be observed in the original trace signal 108.

If a trace signal indicates a failure, then the classification network 306 can further categorize the failure into a failure category depending on a failure cause. For example, if a failure associated with the aspirate probe 202 is detected, the failure can result from a different factor. For instance, the aspirate probe 202 may fail to aspirate any liquid; the aspirate probe 202 may fail to dispense any liquid after aspiration; the pressure sensor 204 may malfunction because no trace signals can be observed. The classification network 306 can categorize the failure into a failure category, in addition to valid or invalid identification 114. In an embodiment, a failure notification will be sent to a system (e.g., an immunoassay and clinical chemistry analyzer) controlling the aspirate probe 202. This failure notification may then be presented on a display for review by an operator or other use. Alternatively, the system may automatically take one or more measures to remediate the failure (e.g., re-aspirate the liquid).

In an embodiment, a plurality of sensors can be provided and connected to the device 102. For example, a pressure sensor, a temperature sensor, and a current sensor are connected to the device 102. Each sensor generates a different trace signal 108, and all the trace signals are input to the machine learning model 106 for analysis.

Although the machine learning model 106 discussed above with reference to FIG. 4 is implemented as a deep neural network, it should be understood that other machine learning models may be utilized in other embodiments of the present invention. Various machine learning models generally known in the art may be utilized including, without limitation, decision tree, gradient-boosted tree, logistic regression, and random forest models.

The machine learning model 106 is trained with a large number of trace signals, with a good sampling of both valid or invalid (i.e., indicative of failure) signals. For example, in one embodiment, the machine learning model 106 is trained with about 80,000 trace signals, including nearly 10,000 trace signals indicative of failures. According to proof of concept testing performed with this training set, the deep neural network can achieve a classification accuracy of 0.9942, which indicates that the failure automatic detection system 100 can effectively detect a failure of a task using sensor trace data.

Figure 6:
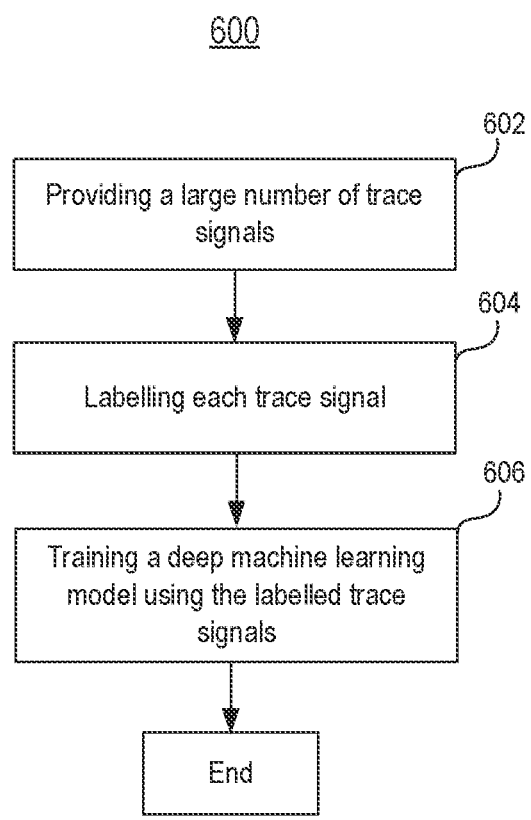
FIG. 6 illustrates a flow chart of a method for training the machine learning model, in accordance with an embodiment described herein.

FIG. 6 illustrates a flow chart of a method 600 for training the machine learning model 106, in accordance with an embodiment described herein. At step 602, a large number of trace signals 108 are provided to train the machine learning model 106. Ideally, the trace signals 108 include a large number of trace signals, with a sampling of valid and invalid trace signals representative of various scenarios under which a corresponding device operates. At step 604, each trace signal 108 is labeled by humans (e.g., machine learning experts with respect to the device 102 and the sensor 104 that generates the trace signal 108). The labeling tags can indicate whether this trace signal 108 is valid or invalid. The labeling tags can also provide other information, for example, the volume aspirated by the aspirate probe 202, the number of aspiration operations, etc. At step 606, the labeled trace signals are input into the machine learning model 106 for training. With supervised learning, the trained machine learning model 106 can identify whether a new trace signal is valid or invalid. The trained machine learning model 106 can further estimate one or more parameters from the new trace signal, such as an estimated volume aspirated by the aspirate probe 202, the estimated number of aspiration operations, etc. The trained machine learning model 106 can further reconstruct the new trace signal, which is compared with the original new trace signal. One or more discrepancies 112 between the reconstructed trace signal and the original new trace signal can be highlighted.

Figure 7:
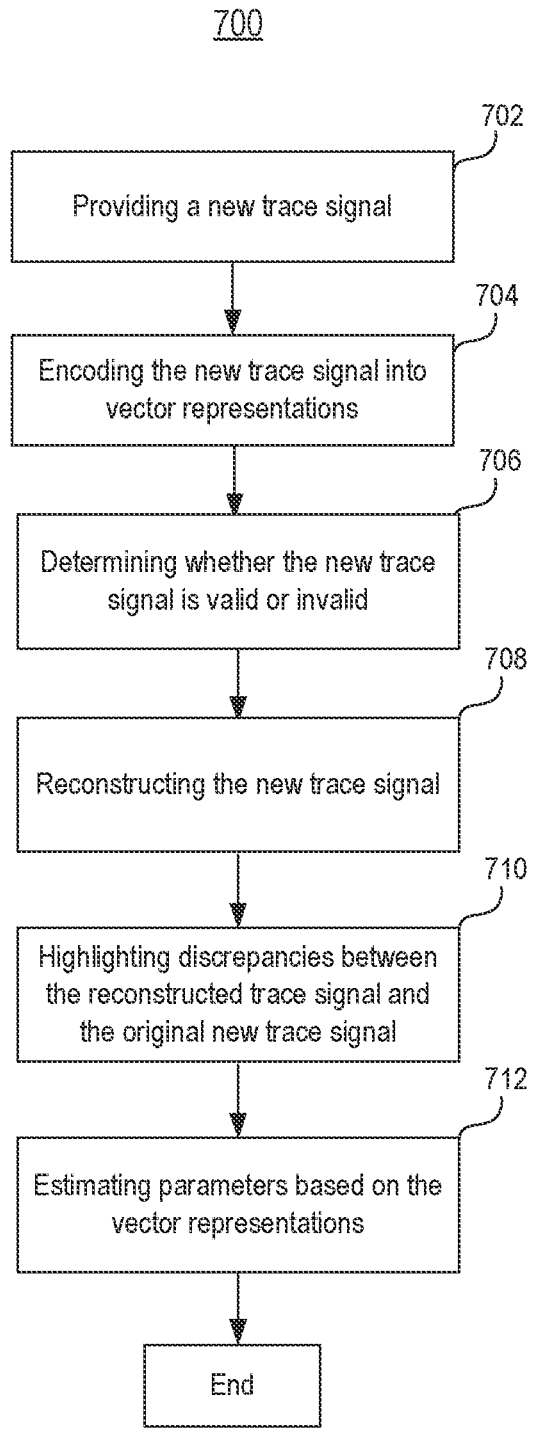
FIG. 7 illustrates a flow chart of a method for detecting a failure of a device, in accordance with an embodiment described herein.

FIG. 7 illustrates a flow chart of a method for detecting a failure of a device 102, in accordance with an embodiment described herein. At step 702, a new trace signal is inputted into the trained machine learning model 106. At step 704, the encoder network 302 in the trained machine learning model 106 encodes the new trace signal into vector representations 310, which form a 64-dimensional manifold in this example. At step 706, the classification network 306 identifies whether the new trace signal is valid or invalid. At step 708, the decoder network 304 reconstructs the new trace signal based on the vector representations 310. At step 710, one or more discrepancies 112 between the reconstructed trace signal and the original new trace signal are highlighted based on the gradients 312 provided by the classification network 306. At step 712, the parameter estimation network 308 estimates one or more parameters (e.g., an estimated volume aspirated by the aspirate probe 202, the estimated number of aspiration operations, etc.) associated with the device 102. The order of steps 706-712 can be randomly adjusted in some embodiments; for example, step 712 can be performed prior to step 706.

Figure 8:
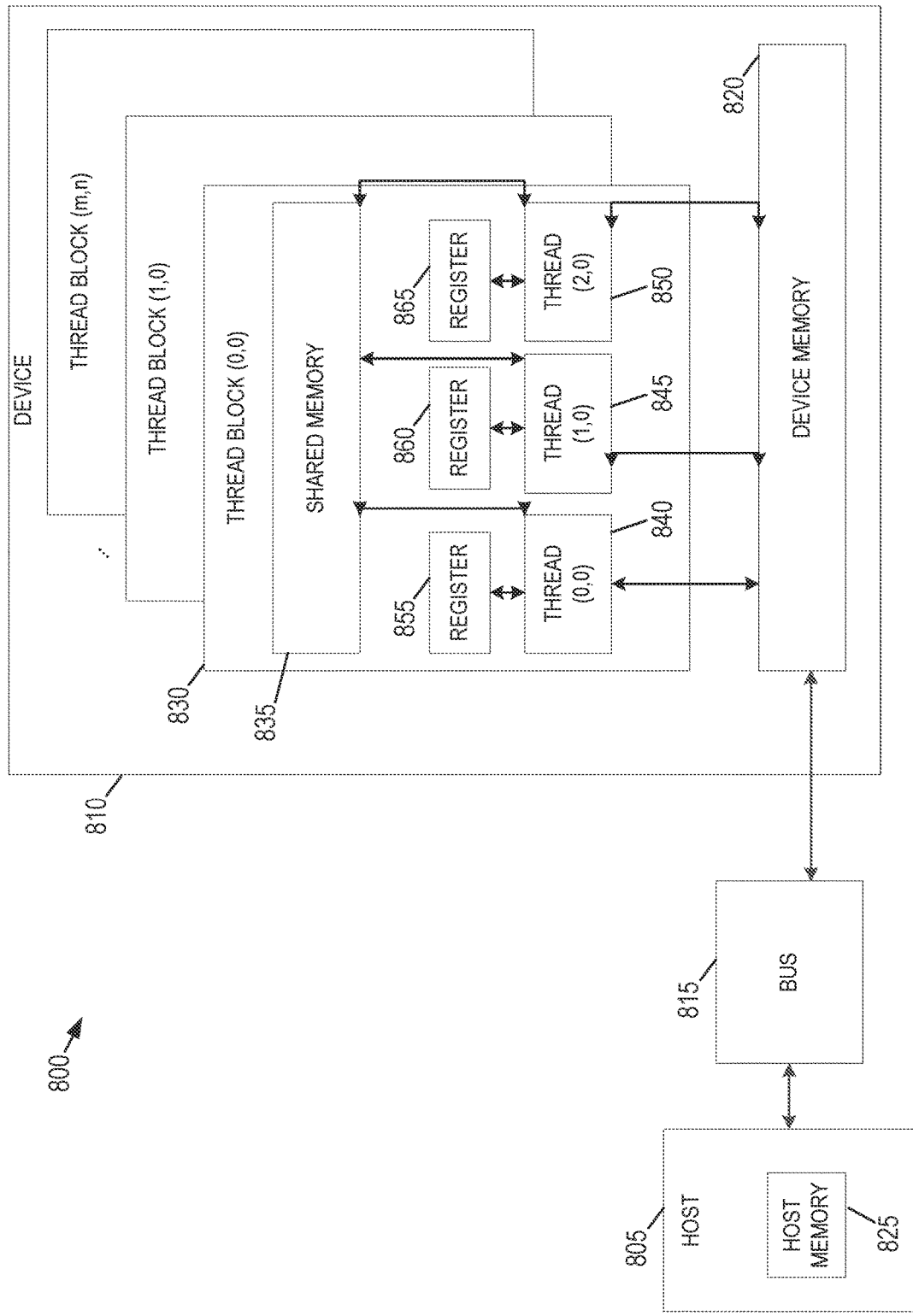
FIG. 8 illustrates an example of a parallel processing memory architecture, in which aspects of the illustrative embodiments are implemented.

FIG. 8 provides an example of a parallel processing memory architecture 800 that may be utilized to implement the machine learning model 106 and other aspects of the various workflows discussed herein. This architecture 800 may be used in embodiments of the present invention where NVIDIA CUDA™ (or a similar parallel computing platform) is used. The architecture includes a host computing unit ("host") 805 and a graphics processing unit (GPU) device ("device") 810 connected via a bus 815 (e.g., a PCIe bus). The host 805 includes a processor or a central processing unit (referred to as "CPU") (not shown in FIG. 8), and host memory 825 accessible to the CPU. The device 810 includes the graphics processing unit (GPU) and its associated memory 820, referred to herein as device memory. The device memory 820 may include various types of memory, each optimized for different memory usages. For example, in some embodiments, the device memory includes global memory, constant memory, and texture memory.

Parallel portions of a big data platform and/or big simulation platform (see FIG. 8) may be executed on the architecture 800 as "device kernels" or simply "kernels." A kernel comprises a parameterized code configured to perform a particular function. The parallel computing platform is configured to execute these kernels in an optimal manner across the architecture 800 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by a grid of thread blocks (described in greater detail below). Using concurrent kernel execution, streams, and synchronization with lightweight events, the architecture 800 of FIG. 8 (or similar architectures) may be used to parallelize portions of the model-based operations performed in training or utilizing the machine learning model discussed herein.

The device 810 includes one or more thread blocks 830 which represent the computation unit of the device 810. The term thread block refers to a group of threads that can cooperate via shared memory and synchronize their execution to coordinate memory accesses. For example, in FIG. 8, threads 840, 845 and 850 operate in thread block 830 and access shared memory 835. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 8, the thread blocks 830 are organized in a two-dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints.

Continuing with reference to FIG. 8, registers 855, 860, and 865 represent the fast memory available to thread block 830. Each register is only accessible by a single thread. Thus, for example, register 855 may only be accessed by thread 840. Conversely, shared memory is allocated per thread block, so all threads in the block have access to the same shared memory. Thus, shared memory 835 is designed to be accessed, in parallel, by each thread 840, 845, and 850 in thread block 830. Threads can access data in shared memory 835 loaded from device memory 820 by other threads within the same thread block (e.g., thread block 830). The device memory 820 is accessed by all blocks of the grid and may be implemented using, for example, Dynamic Random-Access Memory (DRAM).

Each thread can have one or more levels of memory access. For example, in the architecture 800 of FIG. 8, each thread may have three levels of memory access. First, each thread 840, 845, 850, can read and write to its corresponding registers 855, 860, and 865. Registers provide the fastest memory access to threads because there are no synchronization issues and the register is generally located close to a multiprocessor executing the thread. Second, each thread 840, 845, 850 in thread block 830, may read and write data to the shared memory 835 corresponding to that block 830. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 810 to read and/or write to the device memory. Device memory requires the longest time to access because access must be synchronized across the thread blocks operating on the device.

The embodiments of the present disclosure may be implemented with any combination of hardware and software. For example, aside from parallel processing architecture presented in FIG. 8, standard computing platforms (e.g., servers, desktop computers, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer-readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine-readable instructions for conditioning the processor to implement predetermined functions, such as those of an operating system, a context data acquisition system or other information processing system, for example, in response to user command or input. An executable procedure is a segment of code or machine-readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device that displays the image for viewing by the user. The processor, under control of an executable procedure or executable application, manipulates the GUI display images in response to signals received from the input devices. In this way, the user may interact with the display image using the input devices, enabling user interaction with the processor or other devices.

The functions and process steps herein may be performed automatically or wholly or partially in response to a user command. An activity (including a step) performed automatically is performed in response to one or more executable instructions or device operation without user direct initiation of the activity.

The present description and claims may make use of the terms "a," "at least one of," and "one or more of," with regard to particular features and elements of the illustrative embodiments. It should be appreciated that these terms and phrases are intended to state that there is at least one of the particular features or elements present in the particular illustrative embodiment, but that more than one may also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the example provided herein without departing from the spirit and scope of the present invention.

The system and processes of the figures are not exclusive. Other systems, processes, and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes may be implemented using hardware components, software components, and/or combinations thereof. No claim element herein is to be construed under the provisions of 35 U.S.C. 112(f) unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A method for detecting a failure of a device, the method comprising:
   performing, by the device, a task;
   monitoring, by a sensor connected to the device, the performance of the task;
   generating a trace signal based on the monitoring by the sensor;
   receiving, by a machine learning model, the trace signal from the sensor, wherein the trace signal indicates a status of the device;
   encoding, by the machine learning model, the trace signal into a plurality of vector representations; and
   determining, by the machine learning model, whether the trace signal is valid or invalid based on the plurality of vector representations.

2. The method of claim 1, further comprising:
   reconstructing, by the machine learning model, the trace signal; and
   highlighting one or more discrepancies between the reconstructed trace signal and the trace signal in a graphical user interface (GUI).

3. The method of claim 1, further comprising:
   estimating one or more parameters associated with the device based on the plurality of vector representations.

4. The method of claim 3, further comprising:
   regressing the plurality of vector representations to estimate the one or more parameters.

5. The method of claim 1, wherein the plurality of vector representations is included in a 64-dimensional manifold.

6. The method of claim 1, further comprising:
   if the trace signal is invalid,
      identifying, by the machine learning model, a category of the failure.

7. The method of claim 1, wherein the machine learning model is a deep neural network.

8. The method of claim 1, further comprising:
   receiving, by the machine learning model, a plurality of training trace signals from the sensor; and
   receiving, by the machine learning model, one or more labelling tags from a human for each training trace signal, wherein the one or more labelling tags indicate whether each training trace signal is valid or invalid.

9. A method for detecting a failure of an aspirate probe, the method comprising:

performing, by the aspirate probe, an aspiration;
monitoring, by a sensor connected to the aspirate probe, the aspiration;
generating a trace signal based on the monitoring by the sensor;
receiving, by a machine learning model, the trace signal from the sensor, wherein the trace signal indicates a status of the aspirate probe;
encoding, by the machine learning model, the trace signal into a plurality of vector representations; and
determining, by the machine learning model, whether the trace signal is valid or invalid based on the plurality of vector representations;
if the trace signal is invalid,
identifying, by the machine learning model, a category of the failure associated with the aspirate probe.

10. The method of claim 9, further comprising:
reconstructing, by the machine learning model, the trace signal; and
highlighting one or more discrepancies between the reconstructed trace signal and the trace signal in a graphical user interface (GUI).

11. The method of claim 9, further comprising:
regressing, by the machine learning model, the plurality of vector representations to estimate one or more parameters associated with the aspirate probe.

12. The method of claim 11, wherein the one or more parameters include a volume aspirated by the aspirate probe, or a number of aspiration operations.

13. The method of claim 9, wherein the category of the failure is one of no aspiration, no dispensation, and no trace signals.

14. The method of claim 9, wherein the plurality of vector representations is included in a 64-dimensional manifold.

15. A system for detecting a failure of a device comprising:
the device for performing a task;
a sensor connected to the device, the sensor for monitoring the performing of the task; and
a machine learning model to:
encode a first trace signal from the sensor into a plurality of vector representations;
reconstruct the plurality of vector representations into a second trace signal; and
identify whether the first trace signal is valid or invalid.

16. The system of claim 15, wherein the machine learning model can further estimate one or more parameters associated with the device based on the plurality of vector representations.

17. The system of claim 16, wherein the one or more parameters are estimated by regressing the plurality of vector representations.

18. The system of claim 15, wherein the plurality of vector representations is included in a 64-dimensional manifold.

19. The system of claim 15, wherein the machine learning model can further identify one or more discrepancies between the first trace signal and the second trace signal.

20. The system of claim 19, wherein the one or more discrepancies are identified based on the second trace signal and a plurality of gradients output from the machine learning model.

21. The system of claim 20, wherein the device comprises a probe and the task comprises an aspiration.

* * * * *